United States Patent [19]

Kempka

[11] Patent Number: 4,783,813
[45] Date of Patent: Nov. 8, 1988

[54] ELECTRONIC SOUND AMPLIFIER STETHOSCOPE WITH VISUAL HEART BEAT AND BLOOD FLOW INDICATOR

[75] Inventor: Chester W. Kempka, Issaquah, Wash.

[73] Assignee: Lola R. Thompson, Seattle, Wash. ; a part interest

[21] Appl. No.: 946,383

[22] Filed: Dec. 24, 1986

[51] Int. Cl.⁴ .............................................. A61B 7/04
[52] U.S. Cl. .................................................... 381/67
[58] Field of Search .................... 381/67, 72, 158, 12, 381/68, 25, 74, 88, 90; 340/815.11

[56] References Cited

U.S. PATENT DOCUMENTS

| | | |
|---|---|---|
| 2,755,336 | 7/1956 | Zener et al. |
| 3,247,324 | 4/1966 | Cefaly et al. |
| 3,491,750 | 1/1970 | King . |
| 3,525,810 | 8/1970 | Alder . |
| 3,539,724 | 11/1970 | Keesee . |
| 3,555,187 | 1/1971 | Rowley . |
| 3,563,232 | 2/1971 | Webb et al. |
| 3,573,394 | 4/1971 | Birnbaum . |
| 3,586,794 | 6/1971 | Michaelis ............................ 381/158 |
| 3,651,798 | 3/1972 | Egli et al. ............................ 381/67 |
| 3,682,161 | 8/1972 | Alibert . |
| 3,732,868 | 5/1973 | Willems et al. |
| 3,772,478 | 11/1978 | McCabe et al. |
| 3,790,712 | 2/1974 | Andries . |
| 3,829,856 | 8/1974 | Conroy et al. .................. 340/815.11 |
| 3,846,585 | 11/1974 | Slosberg et al. |
| 3,858,005 | 12/1974 | Marshall et al. |
| 3,868,954 | 3/1975 | Ueda . |
| 3,947,646 | 3/1976 | Saito ................................. 381/158 |
| 3,989,895 | 11/1976 | O'Daniel, Sr. |
| 4,008,711 | 2/1977 | Olinger et al. |
| 4,012,604 | 3/1977 | Speidel . |
| 4,048,444 | 9/1977 | Giampapa . |
| 4,058,688 | 11/1977 | Nishimura et al. ................. 381/158 |
| 4,071,694 | 1/1978 | Pfeiffer . |
| 4,072,822 | 2/1978 | Yamada . |
| 4,113,999 | 9/1978 | Swinehart ........................... 381/158 |

(List continued on next page.)

FOREIGN PATENT DOCUMENTS

| | | |
|---|---|---|
| 1466928 | 5/1969 | Fed. Rep. of Germany . |
| 1516418 | 2/1970 | Fed. Rep. of Germany . |
| 1804636 | 5/1970 | Fed. Rep. of Germany . |
| 2113567 | 10/1972 | Fed. Rep. of Germany . |
| 2334320 | 2/1975 | Fed. Rep. of Germany . |
| 2453926 | 5/1976 | Fed. Rep. of Germany . |
| 2646414 | 4/1977 | Fed. Rep. of Germany . |
| 2836188 | 12/1979 | Fed. Rep. of Germany . |
| 2925699 | 1/1981 | Fed. Rep. of Germany . |
| 2929688 | 2/1981 | Fed. Rep. of Germany . |
| 3215277 | 10/1983 | Fed. Rep. of Germany . |
| 3218003 | 11/1983 | Fed. Rep. of Germany . |
| 2330367 | 6/1977 | France . |
| 2429585 | 1/1980 | France . |
| 0158695 | 12/1978 | Netherlands . |
| 2115934 | 9/1983 | United Kingdom . |

OTHER PUBLICATIONS

Biomed Engineering, S9057, (U.S.A.), vol. 12, No. 1, (Jan.–Feb. 1978), (Published Sep. 1978).

Primary Examiner—Forester W. Isen
Attorney, Agent, or Firm—Seed and Berry

[57] ABSTRACT

An electronic sound amplification stethoscope including a battery powered self-contained sound amplification circuit contained in a hand held connector housing inserted in the flexible sound conduit of the stethoscope. The circuit includes a miniaturized microphone for receiving sound waves from the stethoscope pickup head and a miniaturized speaker for transmitting amplified sound waves to the stethoscope headpiece. Both the microphone and speaker may be housed in the connector housing and are vibration insulated from the housing itself. The electronic circuitry and battery power source are located in compartments separated from the microphone and speaker. A LED light source is placed in series between the amplifier circuit and the power source such that the fluctuations in its intensity are directly proportional to the power surges in the circuit. The LED is thus a visual indicator of such body functions as respiration and blood flow. The amplifier circuit is also provided with an on/off volume control thumbwheel located on the surface of the connector housing.

9 Claims, 2 Drawing Sheets

U.S. PATENT DOCUMENTS

| | | |
|---|---|---|
| 4,170,717 | 10/1979 | Walshe . |
| 4,202,348 | 5/1980 | Abe et al. . |
| 4,218,584 | 8/1980 | Attenburrow . |
| 4,220,160 | 9/1980 | Kimball et al. ............... 381/67 |
| 4,224,691 | 9/1980 | Ida ............................. 455/159 |
| 4,254,302 | 3/1981 | Walshe . |
| 4,301,809 | 11/1981 | Pinchak . |
| 4,302,627 | 11/1981 | Inoue . |
| 4,362,164 | 12/1982 | Little et al. . |
| 4,377,727 | 3/1983 | Schwalbach . |
| 4,424,815 | 1/1984 | Kuntz . |
| 4,438,772 | 3/1984 | Slavin . |
| 4,475,559 | 10/1984 | Horn . |
| 4,484,583 | 11/1984 | Graham . |
| 4,498,188 | 2/1985 | Hofer . |
| 4,528,689 | 7/1985 | Katz . |
| 4,528,690 | 7/1985 | Sedgwick . |
| 4,534,058 | 8/1965 | Hower . |
| 4,565,258 | 1/1986 | Butler et al. ............... 381/25 |
| 4,577,638 | 3/1986 | Graham . |
| 4,592,366 | 6/1986 | Sainomoto et al. . |
| 4,594,731 | 6/1986 | Lewkowicz . |
| 4,598,417 | 7/1986 | Deno . |
| 4,602,379 | 7/1986 | Ecklund ............... 381/12 |
| 4,618,986 | 10/1986 | Hower . |
| 4,619,268 | 10/1986 | Uphold et al. . |
| 4,683,587 | 7/1987 | Silverman ............... 381/25 |
| 4,731,849 | 3/1988 | Bloomfield, III ............... 381/67 |

ELECTRONIC SOUND AMPLIFIER STETHOSCOPE WITH VISUAL HEART BEAT AND BLOOD FLOW INDICATOR

BACKGROUND OF THE INVENTION

1. Field of the Invention

The present invention relates to improvements in electronic stethoscopes of the type which include sound amplification and more particularly to a novel housing and component placement for reduction of electronic and acoustical or environmental noise. A visual signal is also produced by the amplifier circuitry which is proportional to the power surges in the amplifier circuit thus providing an efficient and reliable blood flow indication when desired. Although the Stethoscope of the present invention is adaptable for widespread use in the medical field, it has particular advantages when used in medical emergency or medical aid units by doctors or paramedicals who need to immediately determine heartbeat, blood flow or respiratory sounds in an environment with high noise levels. Heartbeat, blood flow and other functions may be detected with a fully clothed patient or accident victim.

2. The Prior Art

In the prior art electronic stethoscopes have been provided with housing structures and component placement such that a high degree of noise interference is experienced. These devices are subjected to interference from the electronic circuitry and from any shock impact or other disturbance to the speaker or microphone housing and by the general environmental noise level. Examples of prior electronic stethoscopes are found in the U.S. Pat. Nos. 2,755,336 to F.B. Zinner et al.; 3,247,324 to R. Cefaly et al.; and 4,254,302 to Walsh. In most of these devices, the problem is compounded by the fact that a sensitive electronic microphone is placed directly in the acoustic transducer portion of the conventional stethoscope structure or is used in lieu thereof. Additionally, insufficient acoustic and electronic insulation is utilized in the electronic component housing and placement of the components is such as to increase rather that limit noise interference. Additionally, adequate provision has not been made to detect such functions as blood flow with visual indication combined with the normal stethoscope function.

SUMMARY OF THE INVENTION

The present invention provides a much improved sound and vibration insulated electronic stethoscope which includes a battery powered amplification circuit. The circuit includes a signal device which is subject to power surges in the amplifier circuit to provide a visual indication of, for example, blood flow or respiratory sounds when the acoustical transducer is located in the chest area or on or near an artery in proximity to the surface of the patient's body. The electronic circuitry, including the microphone and speaker are efficiently housed within a hand graspable housing located in the normal acoustical tubing of the stethoscope. The housing may be held with one hand while the acoustical pickup head is manipulated with the other hand. It may also be possible to locate the microphone within the acoustical tubing between the housing and the acoustical transducer if desired. The housing provides isolated chambers for containing the microphone and the speaker units with provisions being made for complete isolation and insulation of the speaker and microphone units from the housing structure itself. In this manner, the user has a conveniently hand held component housing with indicators and volume control for the amplification circuit. A higher degree of elimination of acoustical and electronic noise is attained by the structure of the housing and placement of the components of the present invention.

The acoustical amplifier and coupler housing of the present invention is compatible with conventional stethoscope designs and may be installed with ease. Since the unit is self contained and does not structurally interfere with either the stethoscope pickup head or the standard head piece, it may simply be inserted into the standard flexible acoustical sound wave conduit without further modification. A miniature microphone receives sound waves from the pickup head via the conduit, the sound is amplified and is directed to the head piece by a miniaturized speaker through the sound wave conduit.

BRIEF DESCRIPTION OF THE DRAWING

Reference is made to the accompanying drawings illustrating preferred embodiments of the invention wherein.

DESCRIPTION OF THE PREFERRED EMBODIMENTS

Figure 1:
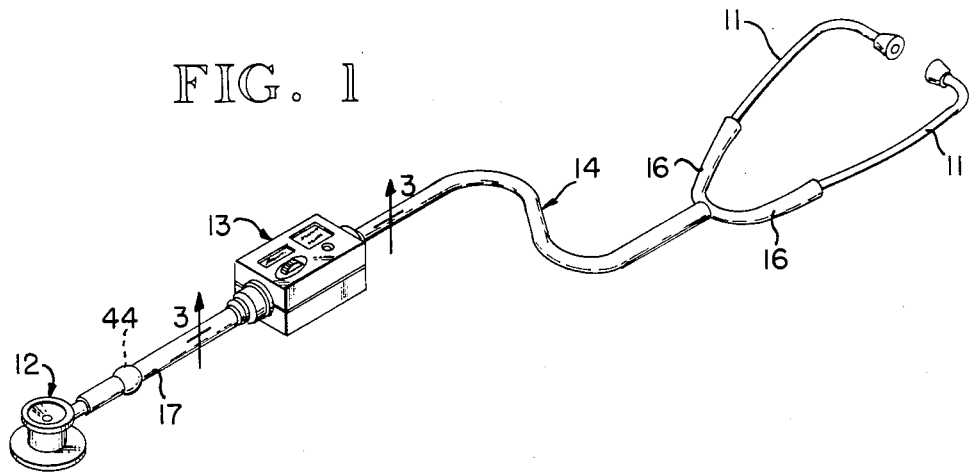
FIG. 1 is an isometric view showing the stethoscope apparatus embodying the invention.
Figure 2:
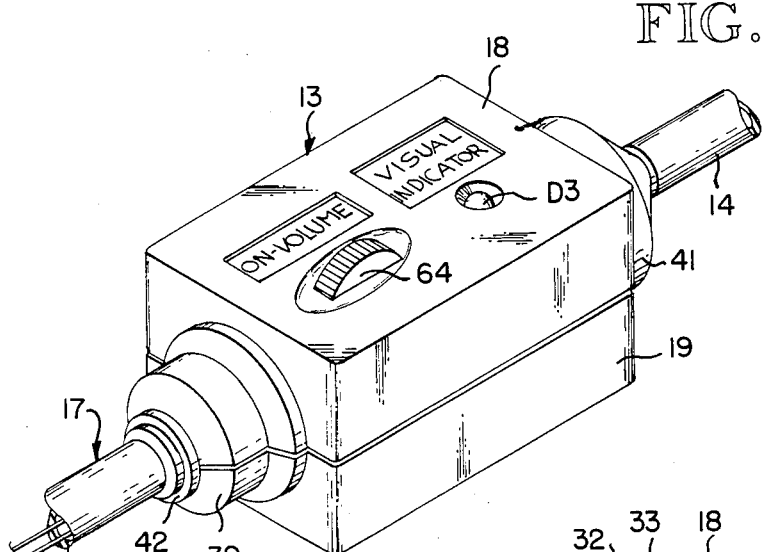
FIG. 2 is a perspective view of the circuitry housing and visual indicators and controls for the apparatus.

Referring in detail to the drawings, FIG. 1 illustrates the composite electronic stethoscope of the present invention which includes a typical binaural headpiece generally indicated at 11—11, a pickup head 12 and a coupler and housing unit 13. The headpiece 11—11 is connected to the coupler 13 by means of conventional hollow flexible acoustic conduit 14 which includes the bifurcated tubes 16—16 connected to the head piece 11—11. The coupler 13 is connected to the acoustical pickup head 12 by means of the flexible acoustical conduit 17.

The binaural headpiece 11—11 and the flexible acoustical conduit or tubing 14 and 16—16 are conventional apparatus well known in the medical arts, the structural details of which form no part of the present invention. The acoustical conduits 14 and 17, and bifurcated end 16—16 may be made from rubber, plastic or other well known flexible tubing and the head piece members 11—11 are normally constructed of metal tubing. The conduit 14, the bifurcated end 16—16 and the head piece members 11—11 serve to transmit acoustical soundwaves from the acoustical pickup apparatus and amplification circuit presently to be described in a well known manner.

The acoustical pickup head 12 may also be of conventional design well known to the medical arts. The acoustical pickup head 12 will normally include a diaphragm and sound chamber type sound transducer which operates to convert acoustical pulses such as those produced by the heart, pulse, blood flow or any other body sounds into audible sound waves within the flexible tubing. The pickup head as is well understood by those skilled in the art is conveniently hand-manipulated with the larger diameter disc being placed against the patient's body or clothing. The structural details of the acoustical pickup head form no part of the present invention. The electronic amplification unit contained in and associated with the coupler housing 13 receives the acoustical waves produced by the transducer of the pickup head.

Figure 3:
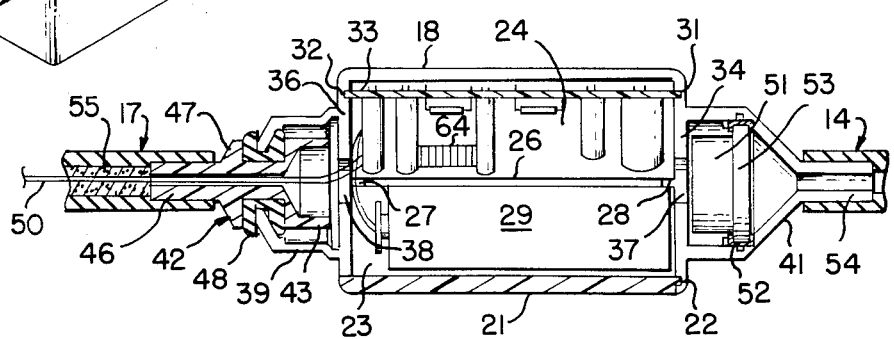
FIG. 3 is a partially sectioned bottom plan view of the housing taken along lines 3—3 of FIG. 1.

The coupler housing 13 serves to connect the two flexible acoustic transmission conduits 14 and 17 and to house the electronic circuitry. The circuitry includes a miniaturized speaker and, in one embodiment, the miniaturized microphone which receives the acoustical sound waves from the pickup head 12. The housing 13 may be manufactured as a two piece unit having the upper and lower housing sections 18 and 19 designed to contain the electronic components. The housing sections will normally be fabricated from a suitable rigid or semi-rigid plastic material with the two halves being held together by adhesive or other securing means once the components and circuitry are installed. In order to gain access to the interior of the housing once the halves are joined, a slidable access panel 21 is received in one pair of the adjoining sidewall portions of the upper and lower housing sections 18 and 19 as shown in FIG. 3. The panel 21 will be provided with edges which engage suitable slots or guides such in the upper and lower housing sections 18 and 19 and with an end edge received in a slot 22.

The housing 13 defines two central chambers 23 and 24 formed by the walls of the housing and a central divider 26, one-half of which may be integrally formed with each half of the housing. Each of the divider wall halves will be provided with notches 27 and 28, one at each end to permit the placement of electrical conduits as will be presently described. The chamber 23 is designed to house the dry cell battery 29 which provides the power source for the amplification circuit. The chamber 24 is provided with slots 31 and 32 in the end walls to accommodate the placement of a circuit board 33 upon which is mounted the solid state components of the electronic amplification circuit as shown in FIG. 3. Access to the battery chamber of course is provided by the panel 21.

Each half of the housing is provided with opposite end walls 34 and 36 which isolate the central chambers 23 and 24. In order to provide for the passage of electrical conduits, each end wall 34 and 36 is provided with a central opening 37 and 38 respectively for a purpose to be described.

A microphone chamber 39 is formed on the end wall 36 and a speaker chamber 41 is formed on the end wall 34. Each chamber 39 and 41 is, of course, comprised of mating cylindrical protrusions on the housing sections 18 and 19 when the housing is fully assembled.

Figure 4:
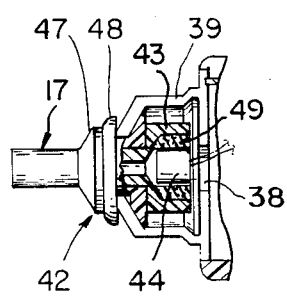
FIG. 4 is a partially sectioned detail of another embodiment of the microphone mounting.

The chamber 39 is provided with a microphone mounting element 42 which includes a microphone socket 43 for mounting a miniaturized microphone 44 as shown in FIG. 4 and an elongated shaft 46 for receiving the open end of the acoustical conduit 17 as shown in FIG. 3. In addition, the shaft 46 is provided with a shoulder 47 for retaining a rubber grommet 48 which fits over the shaft 46 and between the shoulder 47 and the microphone socket 43 to insulate the element 42 from the housing 13 when the two halves of the housing are engaged thereover. The microphone unit 44 may be mounted within the socket 43 and retained therein by means of the annular layer of sound insulation 49. The microphone is thus isolated from the member 42, the housing 13 and also the acoustical conduit 17 as shown in FIG. 4. The chamber 39 is of course isolated from the electronic circuitry except for the passage 38. Alternatively the microphone 44 may be located within the sound conduit 17 as shown in FIGS. 1 and 3 and connected by electrical conduit 50 to the electronic circuitry in the chamber 24 by means of the opening 38 in the end wall 36 as shown in FIG. 3. In this manner the microphone is maintained remote from any electronic interference as a result of the circuitry. In any event, the microphone is isolated from the housing 13 and the rigid mounting element 42. It has also been found that markedly improved results may be obtained by providing a quantity of acoustical and vibration insulation material 55 within the flexible tube 17 between the microphone 44 and the coupler housing 13. The insulation material may comprise any soft natural or synthetic fibrous or cellular material which is loosely packed, flexible and/or resilient. A material should be chosen which does not interfere with the ability to freely manipulate the flexible tube 17. In practice cotton material has been used with success. The placement of sound insulating material 55 is extremely effective in eliminating sound interference and speaker feed back from the housing 13 as the tube 17 is manipulated.

A miniaturized speaker 51 is mounted within the speaker chamber 41 and may also be insulated from the rigid housing by means of the annular sound insulation layer 52 surrounding the rim of the speaker. The layer 52 may comprise plastic or sponge rubber or any suitable resilient vibration insulation material. In the embodiment shown in FIG. 3, the speaker 51 is retained by means of the rim 53 which engages a corresponding annular groove in the housing 41 such that when the housing halves are engaged the speaker is fixed in position. In this manner, the miniaturized speaker 51 is insulated from any shock waves imparted to the housing 13, the acoustical conduit 14 and any environmental noise. Likewise the chamber formed by the housing 41 is isolated from the electronic circuitry except for the passage 37 which allows the passage of electrical conduits connecting the speaker to the circuit board. As shown in FIG. 3, the housing 41 provides the elongated connector 54 for receiving the acoustical conduit 14.

In order to install the amplification circuity including the microphone and speaker, the acoustical conduit of the conventional stethoscope is simply severed to form the portions 14 and 17. The free ends of each engaged conduit portion is then engaged over the corresponding fittings of the microphone and speaker housings. In the event it is desired to locate the microphone within the tubing 17, this may be done by applying a suitable lubricant to the interior of the tube to permit the microphone to be inserted into the hollow tube which is usually composed of soft rubber or plastic. The hollow tube is then provided with a quantity of acoustical insulating material such as cotton as previously described.

Figure 5:
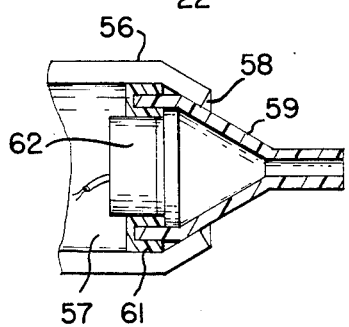
FIG. 5 is a cross sectional detail of an alternate embodiment of the speaker and or microphone mounting in the housing.

FIG. 5 illustrates a modification of the housing structure and acoustical tubing connector which may be utilized for mounting either the microphone unit or the speaker unit. In this modification, the chamber wall 56 will be understood to be composed of the half cylindrical sections of each of the mating housing sections as afore described and the material will be a rigid plastic. The cylindrical chamber 57 formed by the halves of the housing has an open end 58 defined by a bevelled rim wall for the reception within the chamber of the conical shaped conduit connector 59 which has a diameter larger than the diameter of the open end 58 and which will also be constructed of rigid plastic. The connector 59 may be a unitary structure and held in place between the two halves of the housing once they are assembled. The inside end of the connector 59 is provided with an annular grommet 61 which is u-shaped in cross-section and may be made of a soft pliable shock absorbing substance such as soft rubber or other suitable material which serves as a vibration insulator between the connector and the housing walls at its inner end and to receive and insulate the speaker or microphone unit 62. If desired, the speaker or microphone may be adhesively connected to the grommet 61 to insure its retention within the chamber 57. The housing 13 may otherwise be constructed as previously described. The chamber 57 will of course be isolated from the central chambers of the housing 13 as described relative to FIG. 3.

Figure 6:
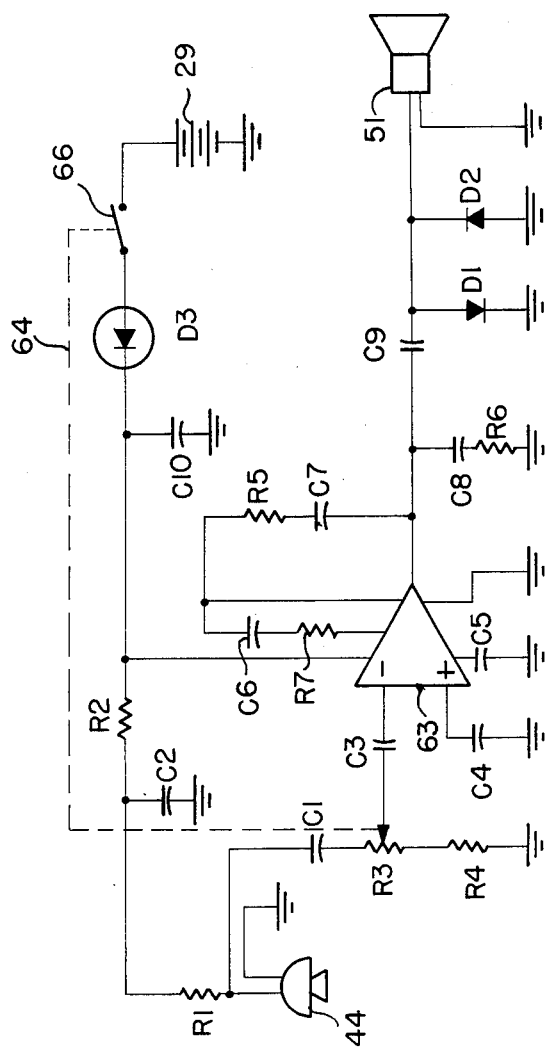
FIG. 6 is an electrical schematic of the sound amplification circuit.

FIG. 6 is an electrical schematic of the sound amplification circuitry. The circuit includes the amplifier unit 63 connected between the two terminal miniaturized microphone 44 and the miniaturized speaker unit 51. The amplifier input on/off and volume control is indicated schematically in FIG. 5 and includes the thumb wheel 64 for operating the on/off switch 66 and the potentiometer assembly volume control R3. The on/off switch 66 serves to connect the DC circuit to the power source 29 which may be a conventional 9 volt battery The volume control R3 controls the amplification of the signals from the microphone 44 and LED light source D3 is inserted in series with the amplifier circuit, the switch 66 and the battery 29. Thus the current flow to the amplifier circuit also energizes the LED such that the intensity of the LED is directly proportional to the volume of sound amplified. The current flow through the LED is responsive to the current fluctuations or power surges in the amplifier and speaker. Except for the placement of the sound intensity responsive LED indicator, the amplifier circuitry may be any conventional circuit capable of performing the function and well known to one skilled in the electrical arts.

The typical circuit elements are indicated as follows:
R-1: 2.2K
R-2: 4.7
R3: 10K
R4: 470 ohm
R5: 4.7K
R6: 10 ohm
R7: 100 ohm
C1: 1 uF-50 Volts
C2: 100 uF 10 V.
C3: 0.1 uF 50 V.
C4: 0.1 uF 50 V.
C5: 0.1 uF 50 V.
C6: 10 uF 16 V.
C7: 0.22 uF 50 V.
C8: 0.1 uF 5 V.
C9: 220 uF 50 V.
C10: 100 uF 10 V.
D1: IN 4148
D2: IN 4148
D3: LED (Light) location in circuit.
44-2 terminal: Microphone
SP1: Speaker 8 ohm dynamic
B1: Battery—9 V alkaline It will be understood from the foregoing description that the present invention provides significant improvements in electronic sound amplification stethoscopes. Although the present invention has been described and illustrated with respect to specific embodiments thereof, it will be apparent to those skilled in the art that modifications to the structures described may be made without departing from the spirit of the invention or from the scope of the appended claims.

What is claimed is:

1. A stethoscope comprising;
sound pickup head,
ear piece,
a connector housing including first and second housing chambers defined by first and second housing chamber walls respectively, with said first housing chamber wall having an edge wall portion defining an opening,
first and second sound transmission conduits connected to said pickup head and said ear piece respectively,
a microphone for receiving sound waves and producing an electronic signal,
a mounting member having a microphone socket portion positioned within said first housing chamber, an elongated mid portion projecting from said socket portion through said first housing chamber opening and a connector end portion positioned exterior of said first housing chamber and sized for attachment of said first conduit thereto, said socket portion having an unperforated annular socket chamber wall defining an interior socket chamber with first and second end openings, said socket chamber wall being spaced apart from and out of contact with said first housing chamber wall to provide a dead air space therebetween, said first socket chamber end opening being sized to receive said microphone therein and said second socket chamber end opening being in communication with an interior sound conductive open channel extending fully through said mounting member from said connector end portion to said socket chamber to transmit sound waves from said first conduit to said socket chamber, said microphone being mounted within said socket chamber so as to detect sound waves communicated therewith only via said sound channel from said first conduit,
first sound and vibration insulating material positioned between said microphone and said socket chamber wall so that in combination with said microphone said first socket chamber end opening is sealed closed, said first material supporting said microphone out of direct contact with said socket chamber wall and providing an airtight seal therebetween such that sound passing through said sound channel is transmitted to said socket chamber and detected by said microphone therein,
a grommet of resilient material positioned within said first housing chamber opening, said grommet having a central opening sized to receive and hold therein said mounting member midportion with said mounting member midportion vibration insulated from said first housing chamber wall,
a speaker mounted in said second housing chamber, said second housing chamber having said second conduit attached thereto for transmission of sound waves generated by said speaker to said ear piece, said speaker being oriented in said second housing chamber so as to transmit sound waves only via said second conduit, second sound and vibration insulating material positioned between said speaker and said second housing chamber walls, and electronic sound amplification means mounted in said connector housing, said sound amplification means including electronic amplifier means and circuit means therefor interconnecting said microphone with said speaker for amplifying said electronic signal and transmitting said amplified electronic signal to said speaker for generating amplified sound waves to said ear piece.

2. A stethoscope comprising:

an interdigitally graspable sound pickup head means, first elongated sound wave transmission conduit means connected to said pickup head means to receive sound waves therefrom, second elongated sound transmission conduit means to receive sound waves ear piece means connected to said second conduit means to receive sound waves therefrom, a connector housing including a central hollow enclosed storage chamber defined by end and side walls and first and second housing chambers formed on the opposite sides of the opposite end walls thereof, said first and second housing chambers being defined by first and second housing chamber walls respectively, with said first housing chamber wall having an edge wall portion defining an opening, microphone means for receiving sound waves and producing an electronic signa, a mounting member having a microphone socket portion positioned within said first housing chamber, an elongated mid portion projecting from said socket portion through said first housing chamber opening and a connector end portion positioned exterior of said first housing chamber and sized for attachment of said first conduit means thereto, said socket portion having an unperforated socket chamber wall defining an interior socket chamber with first and second end openings, said socket chamber wall being spaced apart from and out of contact with said first housing chamber wall to provide a dead air space therebetween, said first socket chamber end opening being sized to receive said microphone means therein and said second socket chamber end opening being in communication with an interior sound conductive open channel extending fully through said mounting member from said connector end portion to said socket chamber to transmit sound waves from said first conduit means to said socket chamber, said microphone means being mounted within said socket chamber so as to detect sound waves communicated therewith only via said sound channel from said first conduit means, first sound and vibration insulation means interposed between said microphone means and said socket chamber wall and completely surrounding the periphery of said microphone means so that in combination with said microphone means said first socket chamber end opening is sealed closed, said first material supporting said microphone means out of direct contact with said socket chamber wall and providing an airtight seal therebetween such that sound passing through said sound channel is transmitted to said socket chamber and detected by said microphone means therein, whereby said microphone means is sound and vibration isolated from said first housing chamber, a grommet of resilient material positioned within said first housing chamber opening, said grommet having a central opening sized to receive and hold therein said mounting member midportion with said mounting member midportion vibration insulated from said first housing chamber wall, speaker means disposed in said second housing chamber, said second housing chamber being connected to said second conduit means for transmission of audible sound waves to said ear piece means, second sound and vibration insulation means interposed between said speaker means and said second housing chamber wall for mounting said speaker means therein oriented so as to transmit audible sound waves from said second housing chamber to said second conduit means only, and electronic sound amplification means mounted in said central chamber, said sound amplification means including electronic amplifier circuit means interconnecting said microphone means with said speaker means for amplifying said electronic signal and transmitting said amplified electronic signal to said speaker means for generating amplified sound waves to said ear piece means.

3. The stethoscope according to claim 2 wherein;

said second insulation means includes sound and vibration insulation means interposed between said speaker means and said second housing chamber completely surrounding the periphery of said speaker means, said speaker means being supported out of direct contact with said second housing chamber wall and sound and vibration isolated from said housing, and wherein said electronic circuit means includes control means having on/off switch means and volume control for said sound amplification means, and activator means for said control means mounted on said housing.

4. A stethoscope comprising;

an interdigitally graspable sound pickup head means, a first elongated elastic and flexible tubing connected to said pickup head means to receive sound waves therefrom, ear piece means, a second elongated elastic and flexible tubing connected to said ear piece means to transmit sound waves thereto, a connector housing including a central hollow enclosed storage chamber defined by end and side walls and by an attachment member and a speaker housing chamber formed on the opposite sides of the opposite end walls thereof, said first tubing being attached to said attachment member and said second tubing being attached to said housing chamber, microphone means for receiving sound waves and producing an electronic signal, said microphone means being mounted interior of said first tubing longitudinally spaced apart from said attachment member and oriented so as to receive sound waves from said pickup head means through said first tubing, said microphone means having a size larger than the unstretched diameter of said first tubing so as to be retained therewithin by the resiliency of the resilient wall of said elastic flexible first tubing, in a fixed position, the resilient wall further serving to sound and vibration insulate the microphone means from environmental noise, speaker means disposed in said speaker housing chamber, said speaker housing chamber being connected to said second tubing for transmission of audible sound waves to said ear piece means, sound and vibration insulation means interposed between said speaker means and said speaker housing chamber for mounting said speaker means therein oriented so as to transmit audible sound waves from said speaker housing chamber to said second tubing only, and electronic sound amplification means mounted in said central chamber, said sound amplification means including electronic amplifier circuit means interconnecting said microphone means with said speaker means for amplifying said electronic signal and transmitting said amplified electronic signal to said speaker means for generating amplified sound waves to said ear piece means, said electronic amplifier circuit means including electrical signal conductors connecting said microphone means in said first tubing to said circuit means via the interior of said first tubing and an interior passage in said attachment member.

5. The stethoscope according to claim 4 further including;

flexible sound insulation material located in said first tubing in the tubing interior space between said microphone means and said attachment member, and substantially filling said tubing interior space therebetween.

6. The stethoscope according to claim 2 wherein said second housing chamber comprises;

a cylindrical enclosure having one end thereof open and the other end thereof comprising one end wall of said connector housing, the open end of said cylindrical enclosure having a bevelled rim wall portion defining an end opening, a conical shaped connector having a reduced diameter end thereof engagable with said second conduit means and the enlarged end thereof positioned within and sized to be engaged by said bevelled rim wall portion of said cylindrical enclosure with said reduced diameter end projecting out of said end opening, said bevelled rim wall portion retaining said conical shaped connector against removal from the cylindrical enclosure through said end opening, said conical shaped connector being hollow with a through passage extending between said reduced and enlarged diameter ends for sound transmission, a U-shaped in cross-section annular resilient grommet positioned on a cylindrical inner rim wall portion of said enlarged diameter end of said conical shaped connector with an inner leg of said grommet on an inward side of said rim wall portion and an outer leg of said grommet on an outward side of said rim wall portion, said speaker means being located within said enlarged diameter end of said conical shaped connector, said outer leg of said grommet being compressed between an inner wall surface of said cylindrical enclosure and said outward side of said rim wall portion and said inner leg of said grommet being positioned between said inward side of said rim wall portion and said speaker means in contact with the periphery of said speaker means, said speaker means being fully surrounded and press fitted against said inner leg of said grommet, whereby said speaker means is sound and vibration insulated from said conical shaped connector and said cylindrical enclosure.

7. In an acoustical stethoscope having sound wave pickup means and ear piece means, an electronic sound amplification means including in combination;

a direct current power source, microphone means for receiving sound waves and producing an electronic signal, speaker means for receiving said electronic signals and producing amplified audible sound waves, electronic amplifier means including circuitry connected to said microphone means, speaker means and power source to amplify said electronic signal from said microphone means and apply said amplified signal to said speaker means, and light emitting means located in said circuitry in series between said power source and said amplifier means, said light emitting means being illuminated with a first lower intensity in response to power from said power source being applied to said circuitry and being illuminated with varying degrees of intensity between said first intensity and a second higher intensity in direct proportion to fluctuations in the magnitude of power surges in said circuitry being supplied to drive said speaker means resulting from the varying amplitude of sound wave pulses received by said microphone means to give a visual indication of power being applied to said circuitry and of the fluctuations in said amplified signal.

8. The stethoscope according to claim 1, wherein said electronic sound amplification means includes;

a direct current power source, and light emitting means located in said amplifier circuit means in series between said power source and said amplifier means, said light emitting means being illuminated with a first lower intensity in response to power from said power source being applied to said amplifier means and being illuminated with varying degrees of intensity between said first intensity and a second higher intensity in direct proportion to fluctuations in the magnitude of power surges in said amplifier means being supplied to drive said speaker resulting from the varying amplitude of sound wave pulses received by said microphone to give a visual indication of power being applied to said amplifier means and of the fluctuations in said amplified electronic signal.

9. The stethoscope according to claim 2 wherein said electronic sound amplification means includes:

a direct current power source, and light emitting means located in said amplifier circuit means in series between said power source and said amplifier means, said light emitting means being illuminated with a first lower intensity in response to power from said power source being applied to said amplifier means and being illuminated with varying degrees of intensity between said first intensity and a second higher intensity in direct proportion to fluctuations in the magnitude of power surges in said amplifier means being supplied to drive said speaker means resulting from the varying amplitude of sound wave pulses received by said microphone means to give a visual indication of power being applied to said amplifier means and of the fluctuations in said amplified electronic signal.

* * * * *

UNITED STATES PATENT AND TRADEMARK OFFICE
CERTIFICATE OF CORRECTION

PATENT NO. : 4,783,813

DATED : November 8, 1988

INVENTOR(S) : Chester W. Kempka

It is certified that error appears in the above-identified patent and that said Letters Patent is hereby corrected as shown below:

In claim 2, column 7, line 23, following "waves" add --,--.

In claim 2, column 7, line 36, delete "signa" and substitute therefor --signal,--.

Signed and Sealed this

Ninth Day of May, 1989

Attest:

Attesting Officer

DONALD J. QUIGG

Commissioner of Patents and Trademarks